United States Patent
Nagai et al.

(10) Patent No.: US 7,442,544 B2
(45) Date of Patent: *Oct. 28, 2008

(54) RECOMBINANT SENDAI VIRUS

(75) Inventors: Yoshiyuki Nagai, Tokyo (JP); Atsushi Kato, Tokyo (JP); Fukashi Murai, Ibaraki (JP); Tsuneaki Sakata, Osaka (JP); Mamoru Hasegawa, Ibaraki (JP); Tatsuo Shioda, Tokyo (JP)

(73) Assignee: Dnavec Research Inc., Ibaraki (JP)

( * ) Notice: Subject to any disclaimer, the term of this patent is extended or adjusted under 35 U.S.C. 154(b) by 360 days.

This patent is subject to a terminal disclaimer.

(21) Appl. No.: 11/130,117

(22) Filed: May 17, 2005

(65) Prior Publication Data

US 2005/0266566 A1    Dec. 1, 2005

Related U.S. Application Data

(63) Continuation of application No. 09/728,207, filed on Dec. 1, 2000, now Pat. No. 7,101,685, which is a continuation of application No. 09/071,591, filed on May 1, 1998, now abandoned.

(51) Int. Cl.
*C12N 15/00* (2006.01)
*A61K 39/155* (2006.01)

(52) U.S. Cl. .................. 435/320.1; 424/211.1

(58) Field of Classification Search .................. None
See application file for complete search history.

(56) References Cited

U.S. PATENT DOCUMENTS

| | | | |
|---|---|---|---|
| 5,166,057 A | 11/1992 | Palese et al. | |
| 5,217,879 A | 6/1993 | Huang et al. | |
| 5,318,898 A | 6/1994 | Israel | |
| 5,445,953 A | 8/1995 | Dorner et al. | |
| 5,578,473 A | 11/1996 | Palese et al. | |
| 5,665,362 A | 9/1997 | Inglis et al. | |
| 5,716,821 A | 2/1998 | Wertz et al. | |
| 5,780,280 A | 7/1998 | Lebkowski et al. | |
| 6,033,886 A | 3/2000 | Conzelmann | |
| 6,231,868 B1 | 5/2001 | Vakharia et al. | |
| 6,514,728 B1 | 2/2003 | Kai et al. | |
| 6,645,760 B2 | 11/2003 | Nagai et al. | |
| 6,723,532 B2 | 4/2004 | Nagai et al. | |
| 6,746,860 B1 | 6/2004 | Tokusumi et al. | |
| 6,828,138 B1 | 12/2004 | Nagai et al. | |
| 7,101,685 B2 * | 9/2006 | Nagai et al. .................. 435/69.1 | |
| 2002/0002143 A1 | 1/2002 | Kano et al. | |
| 2002/0012995 A1 | 1/2002 | Fukumura et al. | |
| 2003/0166252 A1 | 9/2003 | Kitazato et al. | |
| 2003/0170210 A1 | 9/2003 | Masaki et al. | |
| 2003/0170266 A1 | 9/2003 | Kitazato et al. | |
| 2003/0170897 A1 | 9/2003 | Imai et al. | |
| 2004/0005296 A1 | 1/2004 | Yonemitsu et al. | |
| 2004/0053877 A1 | 3/2004 | Fukumura et al. | |
| 2007/0009949 A1 | 1/2007 | Kitazato et al. | |
| 2007/0105208 A1 | 5/2007 | Jun et al. | |
| 2007/0141705 A1 | 6/2007 | Inoue et al. | |
| 2007/0161110 A1 | 7/2007 | Iida et al. | |
| 2007/0248627 A1 | 10/2007 | Iwadate et al. | |
| 2007/0269414 A1 | 11/2007 | Okano et al. | |
| 2008/0014183 A1 | 1/2008 | Okano et al. | |
| 2008/0031855 A1 | 2/2008 | Okano et al. | |
| 2008/0038234 A1 | 2/2008 | Hayashi et al. | |

FOREIGN PATENT DOCUMENTS

| | | |
|---|---|---|
| EP | 0440219 | 1/1991 |
| EP | 0864646 | 9/1998 |
| JP | 4-30791 | 2/1992 |
| JP | 5-85943 | 4/1993 |
| JP | 5-301895 | 11/1993 |
| WO | WO94/08022 | 4/1994 |
| WO | WO96/10400 | 4/1996 |
| WO | WO97/06270 | 2/1997 |
| WO | WO97/41245 | 11/1997 |
| WO | WO2004/038029 | 5/2004 |
| WO | WO 2004/067752 | 8/2004 |

OTHER PUBLICATIONS

Bridgen, A et al., PNAS USA 93: 15400-15404, 1996.
Buchholz, CJ et al., J. Virol. 67:5803-5812, 1993.
Buchholz, CJ et al., Virology 204: 770-776, 1994.
Bukreyev et al., J. Virol. 71: 8973-8982, 1997.
Calain, P. et al., J. Virol. 67:4822-4830, 1993.
Calain, P. et al., Virol. 191: 62-71, 1992.
Calain, P. et al., Virol. 212: 163-173, 1995.
Cameron, E. Mol. Biotech. 7:253-265, 1997.
Chandrika, R. et al., Virology 213: 352-363, 1995.
Collins, PL et al., PNAS USA 88:9663-9667, 1991.
Collins, PL et al., PNAS USA 92: 11563-11567, 1995.
Conzelmann, KK et al., J. Gen. Virol. 77: 381-389, 1996.
Conzelmann, KK et al., Trends in Microbiol. 4: 386-393, 1996.
Conzelmann, KK et al. J. Virol. 68(2): 713-719, 1994.
Curran, J. et al., EMBO J. 10: 3079-3085, 1991.
Curran, J. et al., J. Virol. 67: 4538-4364, 1993.

(Continued)

*Primary Examiner*—Stacy B Chen
(74) *Attorney, Agent, or Firm*—Chalin Smith; Smith Patent Consulting

(57) ABSTRACT

A method for regenerating Sendai virus particles by transfecting the Sendai virus genome to a host expressing all genes for the initial viral replication has been developed, enabling the genetic manipulation of Sendai virus and effective utilization of said virus as the vector.

28 Claims, 3 Drawing Sheets

OTHER PUBLICATIONS

De, BP et al., Virology 196: 344-348, 1993.
De, BP et al., Indian J. Biochem & Biophysics 31: 367-376, 1994.
Delenda, C. et al., Virol. 228: 55-62, 1997.
Domingo, E et al., FASEB J. 10: 859-864, 1996.
Durbin, AP et al., Virology 235: 323-332, 1997.
Durbin, AP et al., Virology 234: 74-83, 1997.
Einberger, H. et al., J. Virol. 64: 4274-4280, 1990.
Garcia-Sastre, A. et al., Ann. Rev. Microbiol. 47:765-90, 1993.
Garcin, D. et al., Virol. 238: 424-431, 1997.
Garcin, D. et al., EMBO J. 14: 6087-6094, 1995.
Ghosh, J. K. et al., Biochem. 36: 15451-15462, 1997.
Gotoh, B. et al., EMBO J 9: 4189-4195, 1990.
Gotoh, B. et al., Virol. 171: 434-443, 1989.
Gupta, KC et al., Biochem. 35: 1223-1231, 1996.
Hahn, CS et al., Proc Natl Acad Sci USA 89(7):2679-83, 1992.
Hamaguchi, M. et al., Virology 128: 105-117, 1983.
Hammer, R. et al., Cell 63:1099-1112 (1990).
Hasan, M. et al., J. Gen. Virol. 78:2813-2820, 1997.
Hill, VM et al., J. Gen. Virol. 71:289-298, 1990.
Homann, HE et al., Virology, 177: 131-140, 1990.
Homann, HE et al., J. Virol. 65: 1304-1309, 1991.
Horikami, SM et al., Virology 235: 261-270, 1997.
Hsu, et al., Virol. 146: 38-49, 1985.
Hurwitz, JL, Vaccine 15: 533-540, 1997.
Kato, A. et al., Genes to Cells 1: 569-579, 1996.
Kato, A. et al., EMBO J. 16: 578-587, 1997.
Kato, A. et al., J. Virol. 71:7266-7272, 1997.
Kido, H. et al., Biol. Chem. 378: 255-263, 1997.
Kondo et al., J. Biol. Chem. 268 (29): 21924-21930.
Lattore, P. et al., J. Virol. 72: 5984-5993, 1998.
Lawson, ND, et al., Proc Natl Acad Sci USA. 92(18):8388-92, 1995.
Luytjes, W. et al., Cell 59:1107-1113, 1989.
Lyles, DS et al., Virology 217: 76-87, 1996.
Malinoski, F. et al., Virology 110:281-291, 1981.
Metsikko, K. et al., J. Virology 63(12): 5111-5118, 1989.
Middleton, et al., Virol. 176: 656-657, 1990.
Mizumoto, K. et al., J. Biochem. 117: 527-534, 1995.
Mottet, G. et al., Virol. 221: 159-171, 1996.
Tuffereau et al., Virology 162: 417-426, 1988.
Whelan, SP et al., Proc Natl Acad Sci USA. 89(7):4477-81, 1995.
Willenbrink, W. et al., J. Virol.., 68: 8413-8417, 1994.
Yonemitsu, Y. et al., Surgery 131(1): S261-268, Jan. 2002.
U.S. Appl. No. 10/532,172, filed Apr. 2005, Okano et al.
U.S. Appl. No. 10/562,408, filed Dec. 23, 2005, Jun You.
U.S. Appl. No. 10/578,085, filed May 3, 2006, Shinji Okano.
U.S. Appl. No. 10/543,734, filed Jul. 29, 2005, Tokusumi et al.
U.S. Appl. No. 09/720,979, filed Mar. 2001, M. Fukumura et al.
U.S. Appl. No. 10/111,356, filed Jul. 2002, Y. Yonemitsu et al.
M. Engelhorn et al., J. Gen. Virol., vol. 74 (Pt 1): 137-41, Jan. 1993.
D. Garcin et al., Virology, vol. 201(1): 19-25, May 15, 194.
SM Horikami et al., J. Virol., vol. 66(8): 4901-8, Aug. 1992.
A. Loyter et al., Exp. Cell Res., vol. 143(2): 415-25, Feb. 1983.
Matusumoto, T., "Assembly of Paramyxoviruses", Microbiol. Immunol. 1982; 26(4): 285-320.
Norby, E. et al., "Humanized Animal Viruses with Special Reference to the Primate Adaptation of Morbillivirus", Vet. Microbiol., Nov. 1992: 33(1-4): 275-86.
Virology Division News: The Order of Mononegavirales, Arch. Virol. 1991; 117(1-2): 137-140.
Moyer, SA et al., PNAS USA 83: 5405-5409, 1986.
Mullins, J. Hypertension 22(4):630-633, 1993.
Nakanishi et al., J. Cell Biochem Suppl. 21A, C6-337, 1995.
Neubert, WJ et al., Virology 125: 445-453, 1983.
Ogura, et al., J. Gen. Virol. 55: 469-473, 1981.
Palese, P. et al., Trends in Microbiol. 3: 123-125, 1995.
Palese, P. et al., PNAS USA 93: 11354-11358, 1996.
Park, KH et al., PNAS USA 88: 5537-5541, 1991.
Park, KH et al., J. Virol. 66: 7033-7039, 1992.
Peavy, D. et al., J. Immunol. 126(3): 861-864, 1981.
Pekosz, A. et al., PNAS USA 96:8804-8806, Aug. 1999.
Radecke, F et al., Virol. 217: 418-421, 1996.
Rolls, MM et al., Virology 218: 406-411, 1996.
Sakaguchi, T et al., J. Gen. Virol. 74: 479-484.
Sakai, Y. FEBS Letters 456:221-226, 1999.
Schnell, J. EMBO Journal 13(18):4195-4203, 1994.
Seidel, G.E., J. Anim. Sci. 71 Suppl 3: 26-33, 1993.
Shioda T et al., Nucleic Acids Research 14: 1545-1563, 1986.
Sigmund, M. et al., J. Virol. Methods 22: 231-238, 1988.
Stricker et al., J. Gen. Virol. 75: 1031-1042.
Takagi, T et al., J. Biochem. 118: 390-396, 1995.
Tanabayashi, K. et al., J. Virol. 70: 6112-6118, 1996.
Tao, T et al., Virology 220: 69-77, 1996.
Tapparel, C. et al., J. Virol. 71: 9588-9599, 1997.
Tashiro, M. et al., J. Virol. 70: 5990-5997, 1996.
Toriyoshi, H. et al., Acids Res. & Human Retroviruses 15(12): 1109-1120, 1999.
Tokusumi, T. et al., Virus Research 86: 33-38, 2002.
Tsimring, LS et al., Physical Review Letters 76: 4440-4443, 1996.

* cited by examiner

Postinfectional time (hrs)

SEQUENCE LISTING

<160> NUMBER OF SEQ ID NOS: 4

<210> SEQ ID NO 1
<211> LENGTH: 38
<212> TYPE: DNA
<213> ORGANISM: Artificial
<220> FEATURE:
<223> OTHER INFORMATION: An artificially synthesized primer sequence

<400> SEQUENCE: 1
tgcggccgcc gtacggtggc aatgagtgaa ggagaagt                38

<210> SEQ ID NO 2
<211> LENGTH: 69
<212> TYPE: DNA
<213> ORGANISM: Artificial
<220> FEATURE:
<223> OTHER INFORMATION: An artificially synthesized primer sequence

<400> SEQUENCE: 2
ttgcggccgc gatgaacttt caccctaagt ttttvttact acggcgtacg tcatcttttt    60
tctctctgc                                                            69

<210> SEQ ID NO 3
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 3
aagcggccgc caaagttcac gatggaagac                30

<210> SEQ ID NO 4
<211> LENGTH: 69
<212> TYPE: DNA
<213> ORGANISM: Artificial
<220> FEATURE:
<223> OTHER INFORMATION: An artificially synthesized primer sequence -continued

```
<400> SEQUENCE: 4
tgcggccgcc atgaactttc accctaagtt tttcttacta cggattatta caatttggac          60
tttccgccc                                                                  69
```

RECOMBINANT SENDAI VIRUS

The present application is a Continuation of U.S. patent application Ser. No. 09/728,207 filed Dec. 1, 2000, now U.S. Pat. No. 7,101,685, which, in turn, is a Continuation of U.S. patent application Ser. No. 09/071,591, filed May 1, 1998, now abandoned, which, in turn, claims priority to PCT/JP96/03069, filed Oct. 22, 1996, which, in turn, claims priority to Japanese application JP 7/285417, filed on Nov. 1, 1995.

FIELD OF THE INVENTION

The present invention relates to the recombinant Sendai virus and the method for preparing the same.

BACKGROUND OF THE INVENTION

Sendai virus is also named hemagglutinating virus of Japan (HVJ), and classified in parainfluenza virus type I, belonging to the genus *Paramyxovirus* of the family Paramyxoviridae.

Sendai virus particle is pleomorphic, having the genome RNA without a function as template for translation (hereafter designated "negative strand RNA") enclosed in an envelope of 150-200 nm in diameter. Historically, Sendai virus has also been regarded as a biotechnologically useful virus, being widely utilized, especially for the production of heterokaryons and hybrid cells, by taking advantage of viral cell-fusion capacity. Also, Sendai virus-based cell fusing liposomes as a vehicle to deliver foreign genes into cells have been developed. Furthermore, Sendai virus is also used as the inducer for various interferons.

According to the classification based on the structure and polarity of genome nucleic acid, RNA viruses are classified into three groups, the double strand RNA viruses (dsRNA virus), positive strand RNA viruses, and negative strand RNA viruses. Sendai virus is a member of this third group (the negative strand RNA viruses). The dsRNA virus group includes reovirus, rotavirus, phytoreovirus, etc., and have segmented, multipartite filamentous dsRNA genomes. Positive strand RNA viruses include poliovirus, Sindbis virus, Semliki forest virus, and Japanese encephalitis virus, which possess a single molecule of positive sense RNA as genome. The genome RNA can function as an mRNA and is capable of producing proteins required for viral RNA replication and particle formation. In other words, the genome RNA itself of positive strand RNA viruses is infectious and capable of disseminating.

In the present specification, by "disseminative capability (spreading capability)" is meant "the capability to form infectious particles or their equivalent complexes and successively disseminate them to other cells following the transfer of nucleic acid into host cells by infection or artificial techniques and the intracellular replication of said nucleic acid. Sindbis virus classified in positive strand RNA viruses and Sendai virus classified in negative strand RNA viruses have both infectivity and disseminative capability. On the other hand, adeno-associated virus classified in the parvovirus family has the infectivity but no disseminative capability (the mixed infection of adenovirus is necessary for the formation of disseminating viral particles). Furthermore, the positive strand RNA derived from Sindbis virus which is artificially transcribed in vitro is disseminative (to form infectious viral particles when transfected into cells). In contrast, not only genomic negative strand but also antigenomic positive strand of Sendai viral RNA artificially transcribed in vitro cannot serve as a functional template to form infectious viral particles when transfected into cells.

Recently, viral vectors have been used as vehicles for gene therapy. In order to use them as gene therapy vectors, it is necessary to establish techniques for reconstituting viral particles. (By "reconstitution of viral particles" is meant the artificial formation of viral genome nucleic acid and the production of original or recombinant viruses in vitro or intracellularly.) This is because, in order to transfer foreign genes into viral vectors, viral particles should be reconstituted from the viral genome with foreign genes integrated by gene manipulation. Once techniques of viral reconstitution are established, it becomes possible to produce viruses with a desired foreign gene introduced, or with desired viral genes deleted or inactivated.

Also, once the viral reconstitution system is constructed and the viral gene manipulation becomes possible, said system appears to become a potential tool for genetically analyzing the viral function. Genetic analysis of viral functions is very important from the medical viewpoint of prevention and therapy of diseases etc. For example, if the replication mechanism of viral nucleic acid is elucidated, by utilizing the differences between said viral metabolism and host-cellular metabolism, it may be possible to develop viricide acting on the viral nucleic replication process and less damaging to host cells. Also, by elucidating functions of viral gene-encoded proteins, it may become possible to develop antiviral drugs targeting proteins related with the viral infectivity and particle formation. Furthermore, by modifying genes concerned with the membrane fusion and preparing liposomes with superior membrane-fusing capability, it will be able to use them as gene therapy vectors. In addition, as represented by the interferon, the viral infection may induce the activation of host genes for viral resistance, resulting in the enhanced viral resistance of hosts. Genetic analysis of virus functions may provide more important information on the activation of host genes.

Reconstitution of DNA viruses possessing DNA as the genomic nucleic acid has been performed for some time, and can be carried out by the introduction of the purified genome itself, such as SV40, into monkey cells [J. Exp. Cell Res., 43, 415-425 (1983)]. Reconstitution of RNA viruses containing an RNA genome has been preceded by positive strand RNA viruses due to the dual function of these genomes as mRNA and the template for replication. For example, in the case of poliovirus, the disseminative capability of the purified genomic RNA itself was already demonstrated in 1959 [Journal of Experimental Medicine, 110, 65-89 (1959)]. Then, it was achieved to reconstitute poliovirus [Science, 214, 916-918 (1981)] and Semliki forest virus (SFV) [Journal of Virology, 65, 4107-4113 (1991)] by the introduction of cloned cDNAs into host cells, which encoded the respective full-length plus strand viral RNAs.

The infectious cycle begins with the viral RNA synthesis from DNA, catalyzed by cellular DNA-dependent RNA polymerase. Furthermore, using these viral reconstitution techniques, gene therapy vectors have been developed [Bio/Technology, 11, 916-920 (1993); Nucleic Acids Research, 23, 1495-1501 (1995); Human Gene Therapy, 6, 1161-1167 (1995); Methods in Cell Biology, 43, 43-53 (1994); Methods in Cell Biology, 43, 55-78 (1994)].

However, as described above, in spite of many advantages of Sendai virus to be biotechnologically and industrially useful virus, its reconstitution system has not been established, because it is a negative-strand RNA. This is due to tremendous difficulty in reconstituting viral particles via viral cloned cDNA because neither genomic nor antigenomic RNA alone expressed from the cDNAs is active as the templates for mRNA synthesis and genome replication. This is absolutely different from the case of positive strand RNA viruses. Although, in JP-A-Hei 4-211377, "methods for preparing cDNAs corresponding to negative strand RNA viral genome and infectious negative strand RNA virus" are disclosed, the entire experiments of said documents described in "EMBO. J., 9, 379-384 (1990) were later found to be not reproducible, so that the authors themselves had to withdraw all the article contents [see EMBO J., 10, 3558 (1991)]. Therefore, it is obvious that techniques described in JP-A-Hei 4-211377 do not correspond to the related art of the present invention. Reconstitution systems of negative strand RNA viruses were reported for influenza virus [Annu. Rev. Microbiol., 47, 765-790 (1993); Curr. Opin. Genet. Dev., 2, 77-81 (1992)]. Influenza virus is a negative strand RNA virus having eight-segmented genomes. According to these literatures, a foreign gene was first inserted into the cDNA of one of said genome segments, and then RNA transcribed from the cDNA containing the foreign gene was assembled with the virus-derived NP protein to form a ribonucleoprotein complex (RNP). Then, cells are transfected with the RNP and further infected with an intact influenza virus, in which the corresponding gene segment does not function under special pressure (such as the presence of neutralizing antibody and high temperature). In cells, gene reassortment occurs to generate a virus in which the genome segment is replaced with the above engineered segment to contain a foreign gene in a small population. This population is then selected and amplified under the pressure described above, thus ultimately generating a desired recombinant virus. Thereafter, the reconstitution of a nonsegmented negative strand RNA virus entirely from cDNA was reported for rabies virus belonging to the *rhabdovirus* family [EMBO J., 13, 4195-4202 (1994)].

Therefore, techniques for reconstituting negative strand viruses have become fundamentally known to the public. However, Sendai virus belongs to the *Paramyxovirus* family, different from the *Rhabdovirus* family. Sendai virus and rabies virus could differ in detailed mechanisms of gene expression and replication. They also differ in protein components and virrion structure. Probably, for their reasons, the direct application of the above-described techniques for rabies virus did not support Sendai virus reconstitution. Also, the reconstitution of viral particles reported on the rhabdovirus was hardly detectable by routine virological procedures such as plaque production on susceptible cell cultures. Furthermore, the yield was not satisfactorily high for practical applications. Besides, in order to provide factors required for the viral reconstitution within host cells, helper viruses such as wild type viruses, recombinant vaccinia virus, etc. were conventionally introduced to host cells together with nucleic acids of the virus to be reconstituted. Accordingly, difficulties in separating the reconstituted desired virus from these harmful viruses were posing a difficult problem.

SUMMARY OF THE INVENTION

An object of the present invention is to establish an efficient system for reconstituting Sendai virus, enabling the gene manipulation of Sendai virus, and providing Sendai viral vector sufficiently useful in the field of gene therapy, etc.

In order to apply to the reconstitution test of Sendai virus, the present inventors first made various investigations using cDNAs encoding the minigenome of Sendai virus. In this minigenome, the entire Sendai virus protein-coding sequence of ca 14 kb is replaced with a reporter gene encoding the fire fly luciferase. This minigenome cDNA is flanked by T7 promoter and hepatitis delta virus ribozyme sequence in a circular plasmid. T7RNA polymerase encoded by a recombinant vaccinia virus was used to drive the plasmid in transfected cells. As a result, the inventors found efficient conditions regarding weight ratios among materials to be introduced into host cells, including the minigenome cDNA, the cDNAs encoding the nucleocapsid protein (N), the large protein (L), and the phosphoprotein (P) and minimizing cytotoxicity induced by the recombinant vaccinia virus to provide the T7RNA polymerase. The N protein derived from cDNA encapsidate the naked viral RNA derived from the minigenome cDNA to form the RNP, which is now active as the template for both viral mRNA synthesis and viral replication, which are also derived from the respective cDNAs. Furthermore, the present inventors obtained full-length cDNAs of both positive and negative strands, constructed plasmids to induce the intracellular biosynthesis of positive strand RNA (antigenome or cRNA) or negative strand RNA (genome or vRNA) of Sendai virus, and transferred said plasmid into host cells expressing N, P, and L proteins from the respective cotransfected plasmids. As a result, the inventors succeeded in reconstituting Sendai virus particles from cDNAs thereof.

That is, the present invention comprises the followings.

1. A recombinant Sendai virus having the genome with a desired foreign gene inserted or a desired viral gene deleted or inactivated, and retaining the disseminative capability.

2. The recombinant Sendai virus of description 1, wherein more than one gene encoding viral functional proteins are modified. In particular, at least one gene encoding a Sendai viral protein selected from the group consisting of NP, P, and L proteins may be deleted or inactivated while all other Sendai viral genes, other than genes encoding NP, P, and L proteins are retained.

3. The recombinant Sendai virus of descriptions 1 or 2 possessing a foreign gene which can be expressed in host cells.

4. A vRNA molecule of the recombinant Sendai viruses of any one of descriptions 1-3.

5. A cRNA molecule of the recombinant Sendai viruses of any one of descriptions 1-3.

6. A kit consisting of the following two components.
   a. a DNA molecule comprising a template cDNA which can transcribe RNAs of descriptions 4 or 5, and
   b. a unit capable of transcribing RNAs of descriptions 4 or 5 with said DNA as template in vitro or intrcellularly.

7. A kit consisting of the following two components.
   a. a host expressing the NP, P, and L proteins of Sendai virus (each protein may be replaced with a protein having an equivalent activity), and
   b. an RNA molecule of descriptions 4 or 5.

8. A method for producing the recombinant Sendai virus of descriptions 1-3, comprising introducing the RNA molecule of descriptions 4 or 5 into host cells expressing the NP, P, and L proteins of Sendai virus (each protein may be replaced by a protein having the equivalent activity).

9. A kit consisting of the following three components,
   a. a host expressing the NP, P, and L proteins of Sendai virus,
   b. a DNA molecule comprising a template cDNA capable of transcribing RNAs or cRNAs of descriptions 4 or 5, and
   c. a unit capable of transcribing vRNAs of descriptions 4 or 5 with said DNA as template in vitro or intracellularly.

10. A method for producing the recombinant Sendai virus of descriptions 1-3, comprising introducing the DNA molecule comprising a template cDNA capable of transcribing RNAs of descriptions 4 or 5, and a unit capable of transcribing RNAs of descriptions 4 or 5 with said DNA as template in vitro or intracellularly into hosts expressing the NP, P, and L proteins of Sendai virus.

11. A method for preparing foreign proteins comprising a process for infecting hosts with the recombinant Sendai virus of description 3, and recovering expressed foreign proteins.

12. A culture medium or allantoic fluid containing expressed foreign proteins obtainable by introducing the recombinant Sendai virus of description 3 into hosts and recovering said culture medium or allantoic fluid.

13. A DNA molecule realizing the expression of a protein encoded by a foreign gene integrated into a Sendai viral vector comprising said foreign gene inserted downstream of a promotor in an orientation for transcribing antisense RNA encoding said protein, and the said promotor.

DETAILED DESCRIPTION OF THE INVENTION

Figure 1:
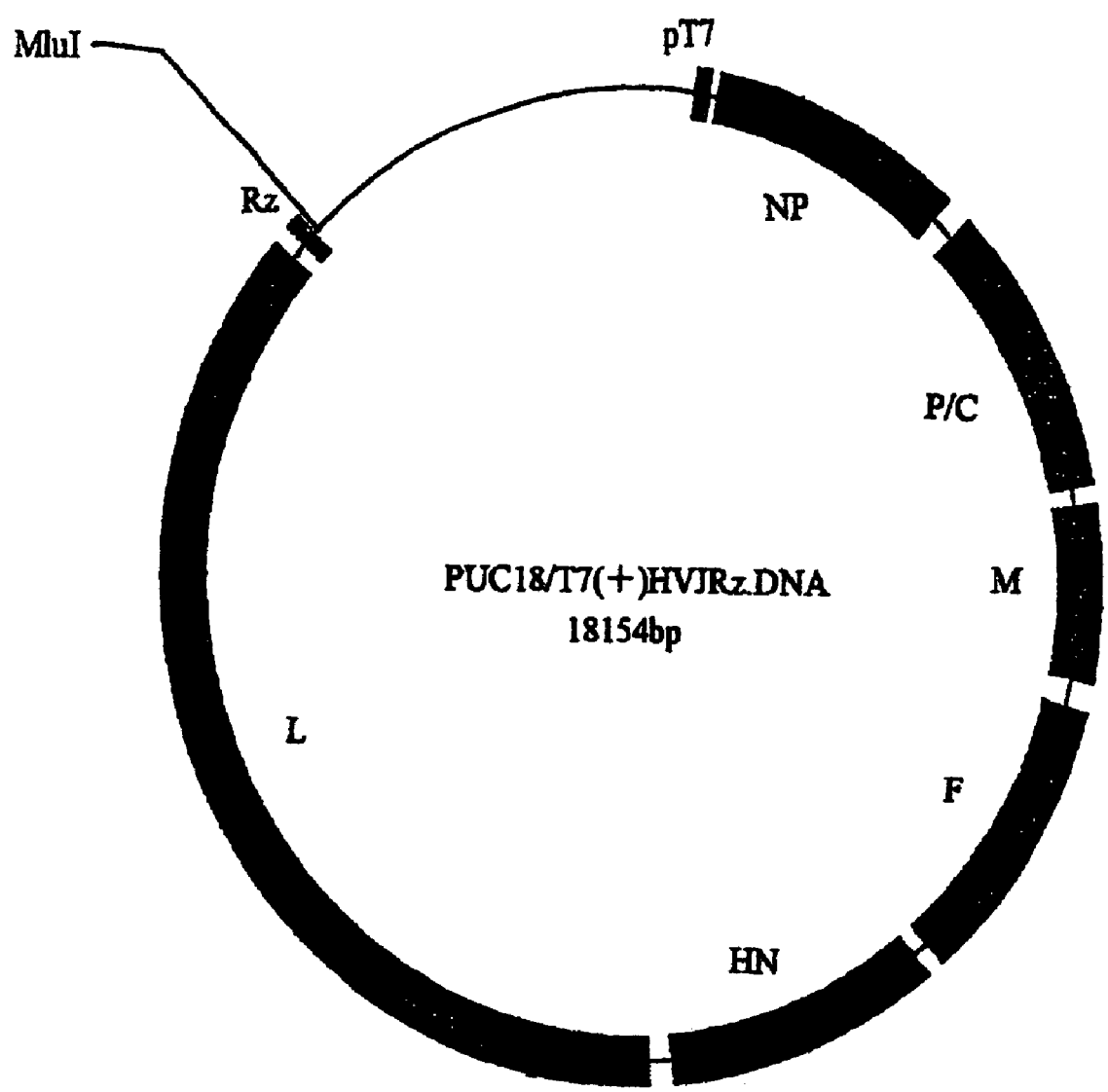
FIG. 1 is a schematic representation of plasmid pUC18/T7 (+)HVJRz.DNA that generates antigenomic sense(+) Sendai virus (HVJ) cRNA.

Sendai virus, the starting material in the present invention for the insertion of a desired foreign gene, or the deletion or inactivation of a desired gene may be a strain classified to parainfluenza virus type I, exemplified by Sendai virus Z strain or Fushimi strain. Furthermore, incomplete viruses such as DI (defective interfering) particles, synthetic oligonucleotides, etc. may be used partial materials.

Recombinant Sendai viral vectors of the present invention can be obtained, for example, by in vitro transcribing the recombinant cDNA encoding the gene-technologically produced recombinant Sendai viral vector genome, producing the recombinant Sendai viral genome RNA, and introducing said RNA to a host simultaneously expressing the NP, P, and L proteins (each protein may be a protein with an equivalent activity) of Sendai virus. Alternatively, Sendai viral vectors of the present invention can be obtained by introducing a) the recombinant cDNA coding for the gene-technologically produced recombinant Sendai viral vector genome, and b) a unit capable of intracellularly transcribing RNA with said DNA as template into a host simultaneously expressing the NP, P, and L proteins (each protein may be a protein having an equivalent activity) of Sendai virus. In this case, said recombinant cDNA a) may be inserted downstream of a specific promotor, and said transcription unit b) may be a DNA molecule expressing a DNA-dependent RNA polymerase acting on said specific promotor.

Sendai virus particles can be reconstituted from its cDNA. The cDNAs introduced into host cells are more preferable in the circular form than in the linear form for the efficient reconstitution of viral particles. Not only the positive strand RNA but also the negative strand RNA can initiate highly successful reconstitution of viral particles although the former is superior to the latter.

Sendai virus reconstitution can be initiated following transfection with full-length viral RNA, either negative or positive sense, that has been synthesized in vitro from the cDNAs. This indicates that, if cells which express all viral proteins (N, P, and L) required for the initial transcription, replication, and encapsidation are constituted, the recombinant Sendai virus can be produced entirely without using helper viruses such as vaccinia virus, and without the expression of heterologous DNA-dependent RNA polymerase. Since cells expressing all the three viral proteins required for the initial transcription, replication, and encapsidation were already described [J. Virology, 68, 8413-8417 (1994)], those skilled in the art will be able to form such complementing cells. The cell type described in said reference is the one derived from the 293 cell line carrying three out of Sendai viral genes, namely N, P, and L on its chromosome, and expressing the proteins encoded by these three genes.

From numerous examples of viral vectors, if viral particles can be efficiently reconstructed from DNAs, it is obvious that those skilled in the art are able to readily exchange desired viral gene, insert a foreign gene, or inactivate or delete a desired viral gene. That is, it will be obvious to those skilled in the art that the first success in reconstituting Sendai viral particles by the present invention has enabled the gene manipulation of Sendai virus.

So far as the recombinant Sendai virus of the present invention maintain the disseminative capability, any foreign gene may be inserted at any site of RNA comprised in said recombinant, and any genome gene may be deleted or modified. Foreign genes to be inserted may be exemplified by genes encoding various cytokines and peptide hormones which can be expressed within hosts. In order to express the desired protein, the foreign gene encoding said desired protein is inserted. In the Sendai viral RNA, it is preferable to insert a sequence of a multiple of 6 nucleotides in length between the sequences R1 (5'-AGGGTCAAAGT-3') and R2 (5'-GTAA-GAAAAA-3') [Journal of Virology, Vol. 67, No. 8 (1993) p. 4822-4830]. Levels of expression of a foreign gene inserted into a vector can be regulated by virtue of the site of gene insertion and the base sequences flanking said foreign gene. For example, Example 5 herein describes the insertion of a foreign gene, gp 120 into a unique NotI restriction site placed before the ORF of the NP gene. In the case of Sendai viral RNA, it is known that there are increasing levels of expression of the inserted gene with decreasing distance of said gene from the promotor at the 3' terminus. Thus, the present invention contemplates the insertion of a foreign gene capable of being expressed in host in the Sendai viral genome prior to the ORF of the NP gene. Preferred hosts for expressing desired proteins may be any cells susceptible to the infection by the recombinant Sendai virus, exemplified by mammalian cells of various tissue-origin in culture and embryonated chicken eggs. It is possible to efficiently produce the foreign gene product by infecting these hosts with the recombinant Sendai virus integrated with expressible foreign gene and recovering the expressed foreign gene product. For example, proteins thus expressed can be recovered by the standard method from the culture medium when cultured cells are the host, and allantoic fluid when chicken eggs are the host.

When a foreign gene is inserted into a plasmid for expressing the negative strand Sendai viral RNA, it is necessary to insert said foreign gene downstream of the promotor in an orientation for transcribing an antisense RNA of said foreign gene encoding a protein. Such "a DNA molecule for expressing a protein encoded by a foreign gene integrated into a Sendai viral vector comprising the foreign gene inserted downstream of the promotor in an antisense orientation for transcribing anisense RNA of said foreign gene encoding said protein and said promotor" has become available for the first time by the present invention, comprising a part of said invention.

Also, for example, in order to inactivate genes for immnogenicity, or enhance the efficiency of RNA transcription and replication, part of genes related with RNA replication of Sendai virus may be modified. Concretely, for example, at least one of the replication factors, the NP, P/C and L proteins may be modified to enhance or reduce the transcription and replication capabilities. The HN protein, one of the structural proteins, has dual activities as hemagglutinin and neuraminidase. For example, the reduction of the former activity may increase the viral stability in blood stream, and the modification of the latter activity may enable the regulation of viral infectivity. Also, the modification of the F protein mediating membrane fusion may be useful for improving membrane fusion liposomes constructed by fusing the reconstituted Sendai virus and artificial liposomes enclosing a desired drug or gene.

The present invention has enabled the introduction of point mutation and insertion at any sites of the genomic RNA, and is highly expected to accelerate the accumulation of genetic information on viral functions. For example, once the mechanism of viral RNA replication is elucidated, it may become possible to develop a viricide less harmful to a host cell and targeting viral replication process by utilizing the differences between viral and cellular metabolisms. In addition, the elucidation of functions of viral gene-encoded proteins may contribute to the development of viricides targeting proteins involved in viral infectivity and reproduction. Concretely, for example, these techniques may be used for the analysis of antigen-presenting epitopes of the F and HN proteins which may act as antigenic molecules on the cell surface. Also, when a host cell gene for viral resistance is activated by viral infection, resulting in an elevated viral resistance, important information on such activation mechanism of host gene may be obtained by the genetic analysis of viral functions. Since Sendai virus is effective in inducing interferons, it is used in various basic studies. By analyzing the genome region necessary for inducing interferons, it may be possible to produce a non-viral interferon inducer. Techniques of the present invention are useful for the development of vaccines. Live vaccines may be produced by inoculating the recombinant Sendai virus with attenuating mutations to embryonated chicken eggs, and can be tested in animals (mice) for protection against the wild-type Sendai virus. Information thus obtained may be applied to other negative strand viruses, such as measles virus and mumps virus, with high demand for live vaccines. Furthermore, the present invention has enabled the usage of the recombinant Sendai virus as vectors for the expression of any prophylactic antigen in body and gene therapy since virus vectors of the present invention derived from Sendai virus are expected to be highly safe in the clinical application, not disseminative in many types of tissues without endogenous proteases required for activation of Sendai virus infectivity, and expected to be therapeutically effective with a relatively small dosage.

In the following, the present invention will be concretely described with reference to Examples, but is not limited to these examples.

EXAMPLE 1

Figure 2:
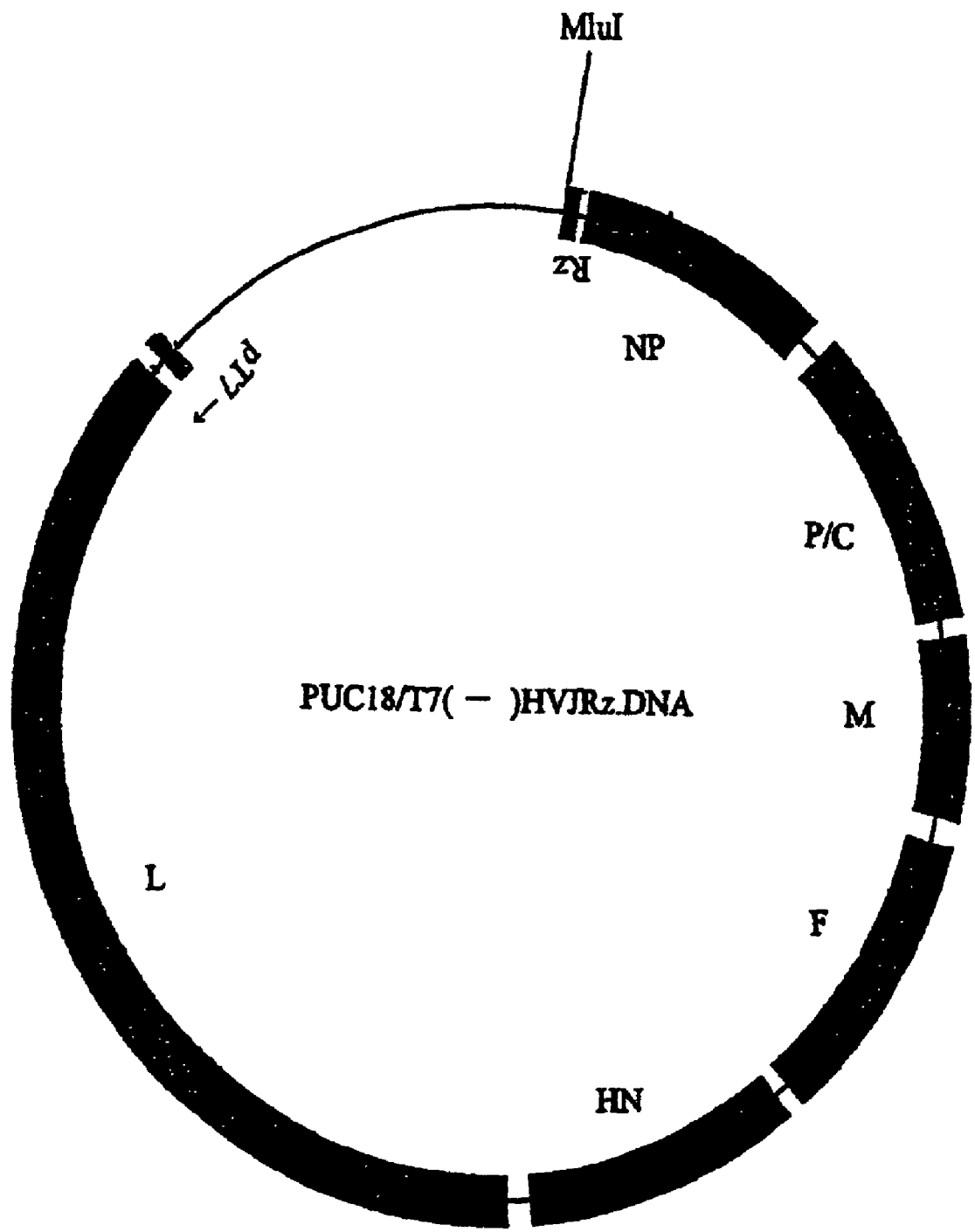
FIG. 2 is a schematic representation of plasmid pUC18/T7 (−)HVJRz.DNA that expresses genomic negative sense(−) vRNA of Sendai virus (HVJ).

Preparation of Sendai Virus cDNA Plasmids,
pUC18/T7(−)HVJRz.DNA and
pUC18/T7(+)HVJRz.DNA Plasmid pUC18/T7(−)HVJRz.DNA was constructed by inserting a DNA molecule comprising T7 RNA polymerase promotor, Sendai virus cDNA designed to be transcribed to the negative strand RNA and the ribozyme gene in this order into pUC18 vector. Also, plasmid pUC18/T7(+)HVJRz.DNA was constructed by inserting a DNA molecule comprising T7 RNA polymerase promotor, Sendai virus cDNA designed to be transcribed to the positive strand RNA and the ribozyme gene in this order into pUC18 vector. Constructions of pUC18/T7(−)HVJRz.DNA and pUC18/T7(+)HVJRz.DNA are shown in FIGS. 1 and 2, respectively.

EXAMPLE 2

Reconstitution Experiment of Sendai Virus from cDNA

LLC-MK2 cells ($2 \times 10^6$) trypsinized in a usual manner were placed in a 60-mm diameter plastic dish, and incubated in MEM medium (MEM supplemented with 10% FBS) (10 ml) in a 5% $CO_2$ atmosphere at 37° C. for 24 h. After removing the medium and washing with PBS (1 ml), a suspension of recombinant vaccinia virus vTF7-3 expressing T7 polymerase in PBS (0.1 ml) was added to the cells at the multiplicity of infection (moi) of 2. The dish was gently agitated every 15 min to thoroughly spread the viral solution for 1 h infection. After removing the viral solution and washing with PBS (1 ml), a medium containing cDNA, which was prepared as follows, was added to the dish.

Nucleic acids shown in Tables 1 and 2 (containing plasmids expressing factors required for the replication of Sendai virus, pGEM-L, pGEM-P, and pGEM-NP were placed in a 1.5-ml sampling tube, and adjusted to a total volume of 0.1 ml with HBS (Hepes buffered saline; 20 mM Hepes pH 7.4 containing 150 mM NaCl). In those tables, (−) and (+)cDNAs represent plasmids pUC18/T7(−)HVJRz.DNA and pUC18/T7(+)HVJRz. DNA, respectively, and /C and /L indicate that cDNA is introduced into cells in the circular form and linear form after digestion of those two plasmids with restriction enzyme MluI, respectively.

On the other hand, in a polystyrene tube were placed HBS (0.07 ml), DOTAP (Boehringer Mannheim) (0.03 ml). To this tube was added the nucleic acid solution described above, and the mixture was left standing as such for 10 min. Then, to this mixture was added the cell culture medium described above (2 ml, MEM supplemented with 10% FBS) followed by the vaccinia virus inhibitors, rifampicin and cytosine arabinoside C (C/Ara/C), to the final concentrations of 0.1 mg/ml and 0.04 mg/ml, respectively, resulting in the preparation of the medium containing cDNA described above.

The dish described above was incubated in a 5% $CO_2$ atmosphere at 37° C. for 40 h. The cells in the dish were harvested using a rubber policeman, transferred to an Eppendorf tube, sedimented by centrifuging at 6,000 rpm for 5 min, and re-suspended in PBS (1 ml). Aliquots of this cell suspension, as such or after diluted, were inoculated to 10-days old developing embryonated chicken eggs. That is, the cell suspension was diluted with PBS to the cell numbers shown in Table 1, and eggs inoculated with its 0.1 to 0.5-ml aliquots were incubated at 35° C. for 72 h, then at 4° C. overnight. Allantoic fluid was recovered as the source of reconstituted virus from these eggs using a syringe with a needle.

Hemagglutinin unit (HAU) and plaque forming unit (PFU) of the recovered virus solution were assayed as follows.

HAU was determined as follows. Chicken blood was centrifuged at 400×g for 10 min and the supernatant was discarded. Precipitates thus obtained were suspended in 100 volumes of PBS, and centrifuged at 400×g for 10 min to discard the supernatant. This procedure was repeated twice to prepare an 0.1% blood cell solution in PBS. Two-fold serial dilutions of virus solutions were prepared, and 0.05 ml each dilution to be assayed was dispensed into each well of 96-well titer plate. The blood cell solution (0.05 ml each) was further added to each well, gently swirled to ensure a thorough mixing, and left at 4° C. for 40 min. The reciprocals of the highest virus dilution to cause the hemagglutination observable with the naked eye was taken as HAU.

PFU was assayed as follows. CV-1 cells were grown to a monolayer on a 6-well culture plate. After the culture medium was discarded, a virus solution 10-fold serially diluted (0.1 ml each) was dispensed into each well of the culture plate to infect the cells at 37° C. for 1 h. During the infection, a mixture of 2×MEM free of serum and melted 2% agar (55° C.) was prepared, and trypsin was added to the mixture to a final concentration of 0.0075 mg/ml. After 1 h infection and removal of the virus solution, the culture medium mixed with agar (3 ml each) was added to each well of the culture plate, and incubated under a 5% $CO_2$ atmosphere at 37° C. for 3 days. Phenol red (0.1%) (0.2 ml) was added to each well, incubated at 37° C. for 3 h, and then removed. Unstained plaques were counted to estimate the virus titer as PFU/ml.

Table 1 shows Sendai virus template cDNAs transfected into LLC-2 cells, amounts of cDNA factors, pGEM-L, pGEM-P, and pGEM-NP, required for the RNA replication incubation time, cell numbers inoculated to chicken eggs, HAU and PFU values recovered into the allantoic fluid.

These results demonstrated that Sendai virus can be reconstituted by introducing cDNAs into cells, and that virus particles are more efficiently reconstituted by introducing cDNAs transcribing positive strand RNAs as compared with those transcribing negative strand RNAs, and further by introducing cDNAs in the circular form rather in the linear form. The coexisting vaccinia virus in an amount of ca $10^4$ PFU/ml in the allantoic fluid was readily eliminated by the virus once again in eggs at a dilution of $10^{-7}$ or $10^{-8}$. This limiting dilution protocol was used to prepare vaccinia-free stock of recovered Sendai virus in this and all subsequent studies.

EXAMPLE 3

Survey of RNA Replication Factors Required for Sendai Virus Reconstitution

Experiments were performed to examine whether all three plasmids expressing the L, P, and NP proteins were required for the reconstitution of Sendai virus. Experimental methods were similar to those described in Example 2 except that any combinations of two out of pGEM-L, pGEM-P, and pGEM-NP plasmids or only one out of them, instead of all these three combined as in Example 2, were introduced together with a template cDNA into cells.

Table 2 shows Sendai virus template cDNAs introduced into LLC-MK2 cells, amounts of the cDNA plasmids required for RNA replication in trans, incubation time, number of cells inoculated into chicken eggs, and values of HAU and PFU.

TABLE 1

| Template cDNA | amount (μg) | pGEM-L (μg) | pGEM-P (μg) | pGEM-NP (μg) | Incubation time (h) | Amount of cells | HAU | PFU |
|---|---|---|---|---|---|---|---|---|
| (+)cDNA/C | 10 | 4 | 2 | 4 | 40 | $1.00 \times 10^5$ | 512 | $2 \times 10^9$ |
| (+)cDNA/C | 10 | 4 | 2 | 4 | 40 | $1.00 \times 10^5$ | 256 | $9 \times 10^8$ |
| (+)cDNA/C | 10 | 4 | 2 | 4 | 40 | $1.00 \times 10^6$ | 256 | $9 \times 10^8$ |
| (+)cDNA/L | 10 | 4 | 2 | 4 | 40 | $1.00 \times 10^5$ | <2 | <10 |
| (+)cDNA/L | 10 | 4 | 2 | 4 | 40 | $1.00 \times 10^5$ | <2 | <10 |
| (+)cDNA/L | 10 | 4 | 2 | 4 | 40 | $1.00 \times 10^6$ | <2 | <10 |
| (−)cDNA/L | 10 | 4 | 2 | 4 | 40 | $1.00 \times 10^4$ | <2 | <10 |
| (−)cDNA/L | 10 | 4 | 2 | 4 | 40 | $1.00 \times 10^5$ | <2 | <10 |
| (−)cDNA/L | 10 | 4 | 2 | 4 | 40 | $1.00 \times 10^6$ | <2 | <10 |
| (−)cDNA/C | 10 | 4 | 2 | 4 | 40 | $1.00 \times 10^4$ | <2 | <10 |
| (−)cDNA/C | 10 | 4 | 2 | 4 | 40 | $1.00 \times 10^5$ | <2 | <10 |
| (−)cDNA/C | 10 | 4 | 2 | 4 | 40 | $1.00 \times 10^6$ | 4 | $8 \times 10^3$ |

Samples showing both HAU and PFU were sedimented by ultra-centrifugation, re-suspended, purified by a sucrose density gradient centrifugation from 20% to 60%. The viral proteins of thus purified virions were fractionated by 12.5% SDS-PAGE. Each viral protein recovered from cDNAs samples was the same in size as that of the conventional Sendai virus.

TABLE 2

| Template cDNA | amount (μg) | pGEM-L | pGEM-P | pGEM-NP | Incubation time (h) | Number of cells inoculated | HAU | PFU |
|---|---|---|---|---|---|---|---|---|
| (+)cDNA/C | 10 | 4 | 2 | 4 | 40 | $1.00 \times 10^5$ | 256 | $6 \times 10^8$ |
| (+)cDNA/C | 10 | 4 | 2 | 4 | 40 | $1.00 \times 10^6$ | 512 | $4 \times 10^9$ |
| (+)cDNA/C | 10 | 0 | 2 | 4 | 40 | $1.00 \times 10^6$ | <2 | <10 |

TABLE 2-continued

| cDNA | Template amount (μg) | pGEM-L | pGEM-P | pGEM-NP | Incubation time (h) | Number of cells inoculated | HAU | PFU |
|---|---|---|---|---|---|---|---|---|
| (+)cDNA/C | 10 | 0 | 2 | 4 | 40 | $1.00 \times 10^6$ | <2 | <10 |
| (+)cDNA/C | 10 | 4 | 0 | 4 | 40 | $1.00 \times 10^6$ | <2 | <10 |
| (+)cDNA/C | 10 | 4 | 0 | 4 | 40 | $1.00 \times 10^6$ | <2 | <10 |
| (+)cDNA/C | 10 | 4 | 2 | 0 | 40 | $1.00 \times 10^6$ | <2 | <10 |
| (+)cDNA/C | 10 | 4 | 2 | 0 | 40 | $1.00 \times 10^6$ | <2 | <10 |
| (+)cDNA/C | 10 | 0 | 0 | 4 | 40 | $1.00 \times 10^6$ | <2 | <10 |
| (+)cDNA | 10 | 0 | 0 | 4 | 40 | $1.00 \times 10^6$ | <2 | <10 |
| (+)cDNA/C | 10 | 0 | 2 | 0 | 40 | $1.00 \times 10^6$ | <2 | <10 |
| (+)cDNA/C | 10 | 0 | 2 | 0 | 40 | $1.00 \times 10^6$ | <2 | <10 |
| (+)cDNA/C | 10 | 4 | 0 | 0 | 40 | $1.00 \times 10^6$ | <2 | <10 |
| (+)cDNA/C | 10 | 4 | 0 | 0 | 40 | $1.00 \times 10^6$ | <2 | <10 |

As shown in Table 2, no virus reconstitution was observed by introducing any combinations of two out of these three factors into cells, confirming the necessity of all three proteins L, P, and NP for the virus reconstitution.

EXAMPLE 4

Reconstitution Experiment of Sendai Virus In Vitro from Transcribed RNAs

Since the reconstitution of Sendai virus from the functional cDNA clones was described in Example 2, it was further examined whether transcription products of said cDNAs in vitro, that is, v or (−)RNA and c or (+)RNA, can initiate and support similar reconstitution.

After the Sendai virus cDNA plasmids, pUC18/T7(−)HVJRz.DNA and pUC18/T7(+)HVJRz.DNA, were linearized with restriction enzyme MluI, using these DNAs as templates, RNA synthesis was performed in vitro with a purified T7 polymerase preparation (EPICENTRE TECHNOLOGIES: Ampliscribe T7 Transcription Kit). The method for synthesizing in vitro RNAs essentially followed the protocols provided with the kit. Using RNA products thus obtained in place of cDNAs in Example 2, similar experiments were performed, and the virus production was estimated by HA test. Results are shown in Table 3.

These results indicate that virus can be reconstituted by introducing either negative or positive sense strand RNAs into cells.

EXAMPLE 5

Expression of Foreign Genes Inserted into Sendai Viral Vectors in Host Cells

1. Preparation of Sendai virus vector "pSeVgp120" inserted with a foreign gene, the gp120 of human immunodeficiency virus type 2 (HIV)

Using a set of primers comprising primer a (5′-TGCGGC-CGCCGTACGGTGGCAATGAGTGAAGGAGAAGT-3′) (SEQ ID NO:1) and primer d (5′-TTGCGCCCGCGAT-GAACTTTCACCCTAAGTTTTTTATTACTACGGCG-TACGTCATCTTTTTTCTCTCTGC-3′) (SEQ ID NO:2), the HIV-1gp120 gene was amplified on "pN1432" or a full-length cDNA of HIV-1 strain NL43 by the standard PCR techniques. PCR products were subjected to TA cloning, digested with NotI, and then inserted into the NotI site of "pSeV18+". pSeV18+ contains an additional 18 nucleotide sequence with a unique NotI restriction site which is placed before the ORF of NP gene of pUC/T7(+)HVJRz. Then, E. coli cells were transformed with this recombinant plasmid. DNAs were extracted from each colony of E. coli by the

TABLE 3

| cDNA | Template amount (μg) | pGEM-L (μg) | pGEM-P (μg) | pGEM-NP (μg) | Incubation time (h) | Number of cells inoculated | HAU | PFU |
|---|---|---|---|---|---|---|---|---|
| in vitro (−)RNA | 10 | 4 | 2 | 4 | 40 | $1.00 \times 10^6$ | 512 | $2 \times 10^9$ |
| in vitro (−)RNA | 10 | 4 | 2 | 4 | 40 | $1.00 \times 10^6$ | 512 | ND |
| in vitro (+)RNA | 10 | 4 | 2 | 4 | 40 | $1.00 \times 10^6$ | 2 | $5 \times 10^3$ |
| in vitro (+)RNA | 10 | 4 | 2 | 4 | 40 | $1.00 \times 10^6$ | <2 | ND |

"Miniprep" method, digested with DraIII, and then electrophoresed. Positive clones (designated "clone 9" hereafter) were selected by confirming to contain DNA fragments of the size expected from the insertion. After DNA fragments were confirmed to have the authentic nucleotide sequence, DNAs were purified by a cesium chloride density gradient centrifugation. pSeV18+ inserted with the gp120 gene is designated "pSeVgp120 " hereafter.

2. Reconstitution of Sendai virus containing pSeVgp120 (SeVgp120) and analysis of gp120 expression Reconstitution of the virus from pSeVgp120 in LLCMK2 cells, the virus recovery from allantoic fluid of embryonated chicken eggs, and assay of the viral HAU were done exactly as described in Example 2. The recovered virus was also examined for the expression of gp120 by ELISA as follows.

Samples (100 μl each allantoic fluid) were dispensed into each well of a 96-well plate which had been coated with monoclonal antibody against HIV-1, and incubated at 37° C. for 60 min. After washing with PBS, HRP-linked anti-HIV-1 antibody (100 μl each) was added to each well, and incubated at 37° C. for 60 min. After washing with PBS, tetramethylbenzidine was added to each well, and amounts of reaction product converted by the action of HRP under acidic conditions were determined by following the optical density at 450 nm to estimate the expression amount of gp120. Results are shown in the left-hand column in Table 4.

The virus solution thus obtained was inoculated to CV-1 cells, and similarly examined for gp120 expression as follows. CV-1 cells were dispensed to a culture plate at $5 \times 10^5$ cells/plate, grown, and then the culture medium was discarded. After washing with PBS(-), the viral solution was added to the cells at the multiplicity of infection of 10, and incubated at 37° C. for 1 h. After the virus solution was discarded, washed with PBS(-), a plain MEM medium (MEM medium supplemented with antibiotics AraC and Rif, and trypsin) was added to the cells, and incubated at 37° C. for 48 h. After the reaction, the medium was recovered and assayed for HAU (by a similar method as described in Example 2) and examined for the expression of gp120 (by ELISA). Results are shown in the center column of Table 4. In addition, the supernatant of CV-1 cell culture medium was inoculated to embryonated chicken eggs again, and the virus solution thus obtained was assayed for HAU and also examined for the gp120 expression (by ELISA). Results are shown in the right hand column of Table 4.

TABLE 4

| Allantoic fluid (F1) gp120 (HAU) | CV-1 medium (F1) gp120 (HAU) | (μg/ml) Allantoic fluid (F2) gp120 (HAU) |
|---|---|---|
| 0.10 (4) | 3.46 (128) | |
| 0.15 (32) | 1.81 (128) | 1.56, 1.21 (512, 512) |
| 0.05 (32) | 2.20 (128) | |

As shown in Table 4, markedly high concentrations of gp120 were detected in CV-1 cells in culture (center column of the Table), and also in the allantoic fluids from embryonated chicken eggs inoculated again with the virus (right-hand column of the Table). In the left-hand and center columns of the Table are shown the mean values of three clones.

Furthermore, the expression of gp120 was analyzed by Western blotting. After the culture medium of CV-1 cells infected with SeVgp120 was centrifuged at 20,000 rpm for 1 h to sediment virus, the supernatant was treated with either TCA (10%, v/v) for 15 min on ice or 70% ethanol at −20° C., and centrifuged at 15,000 rpm for 15 min. Proteins thus precipitated were solved in an "SDS-PAGE sample buffer" (Daiichi Chemicals) at 90° C. for 3 min, and then subjected to electrophoresis on 10% SDS-polyacrylamide gel (SDS-PAGE). Proteins thus fractionated were transferred to PVDF membranes (Daiichi Chemicals), reacted with monoclonal antibody 902 at room temperature for 1 h, and then washed with T-TBS. The membranes were reacted with anti-mIgG (Amersham) at room temperature for 1 h, and washed with T-TBS. The membranes were then reacted with HRP-linked protein A (Amersham) at room temperature for 1 h, washed with T-TBS, and 4-chloro-1-naphthol (4CNPlus) (Daiichi Chemicals) was added to detect gp120. As a result, protein bands were visualized at positions corresponding to the expected molecular weight of gp120.

Figure 3:
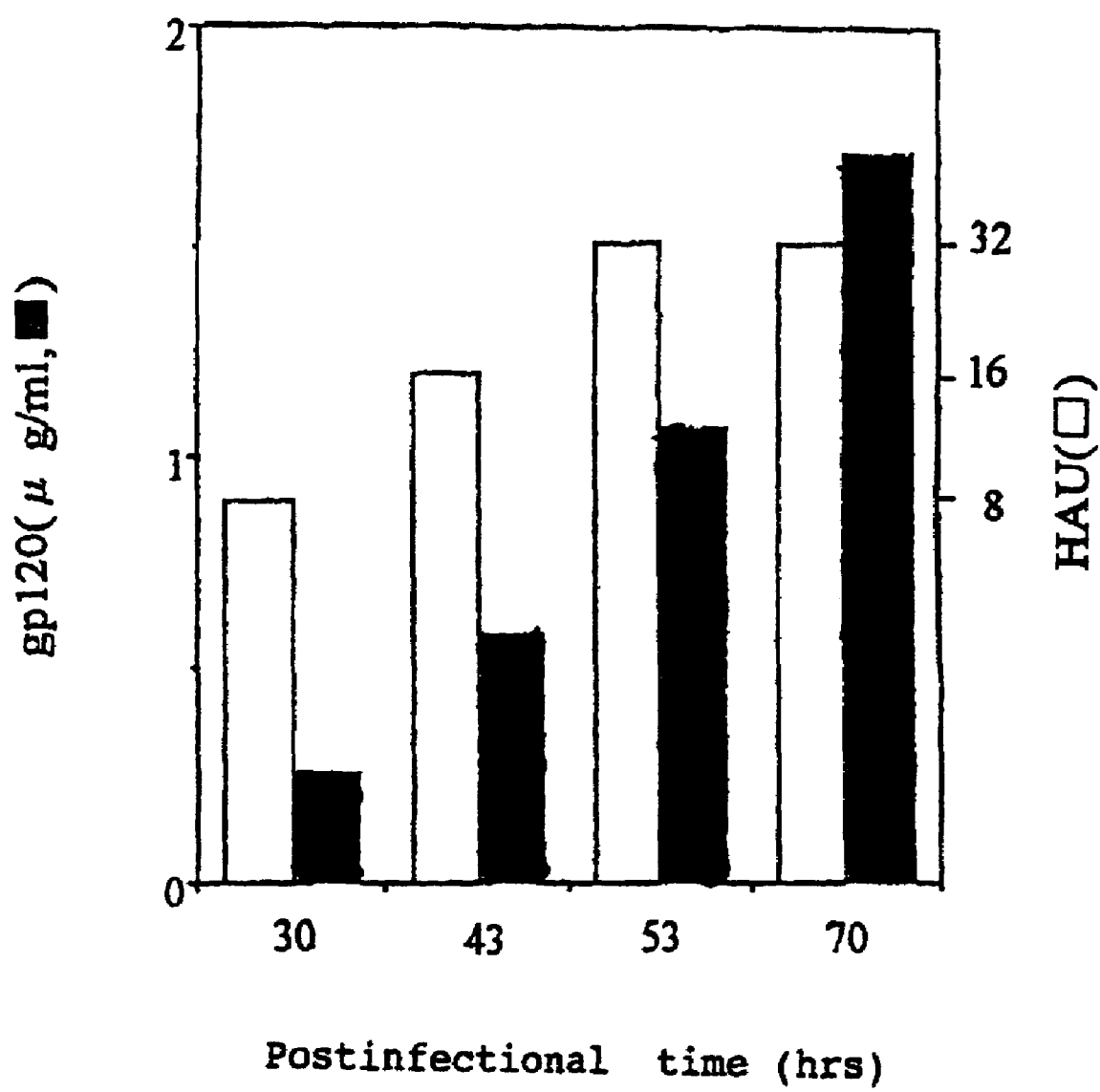
FIG. 3 is a graphic representation of the relationship between the postinfection time of CV-1 cells with SeVgp120 and HAU (the recombinant Sendai virus titer) as well as the expression level of the gp120 of human immunodeficiency virus type 1.

In addition, effects of postinfection time of CV-1 cells transfected with SeVgp120 on the HAU value and gp120 expression amount were analyzed. CV-1 cells ($5 \times 10^6$) dispensed to 10-cm plate were infected with SeVgp120 at the multiplicity of infection of 10, and the culture medium (1 ml each) was postinfectionally recovered at 30, 43, 53 and 70 h, mixed with an equal volume of the fresh medium, and subjected to HAU assay, gp120 expression examination (by ELISA) and Western blotting. Results are shown in FIG. 4. As clearly shown in FIG. 3, the production of gp120 tends to increase with the increasing HA titer of Sendai virus.

EXAMPLE 6

Analyses of SeVgp120 Propagation and gp120 Production in Various Types of Cells

Using similar methods as those in Example 5 except for the use of various types of cells, HAU and gp120 expression levels (by ELISA) were assayed. Results are shown in Table 5.

TABLE 5

| Cell type | Hours (postinfection) | HAU | rgp120 (μg/ml) |
|---|---|---|---|
| CV-1 | 96 | 32 | 2.5 |
| LLCMK2 | 48 | 16 | 0.5 |
| CHO | 55 | 4 | 0.46 |
| NIH3T3 | 48 | 4 | 0.25 |
| MT4 | 24 | 16 | 0.8 |
| MOLT4/ | 24 | 16 | 1.2 |

In the left-hand column of the Table are shown the postinfection times (hours) of various types of cells transfected with SeVgp120. As a result, SeVgp120 propagation and gp120 expression were detected in all types of cells tested.

EXAMPLE 7

Studies on the Expression of Luciferase Gene Inserted Into the Sendai Viral Vector in Host Cells In order to isolate the luciferase gene for inserting to vectors, the luciferase gene bounded by the engineered NotI sites on both termini was constructed by the standard PCR using a set of primers [5'-AAGCGGCCGCCAAAGTTCACGATG-GAAGAC-3') (30mer) (SEQ ID NO: 3)] and [5'-TGCGGC-CGCGATGAACTTTCACCC-TAAGTTTTTCTTAC-TACGGATTATTACAAATTTGGACTTTCCGCCC-3' (69mer) (SEQ ID NO: 4) with the minigenome encoding plasmid, "pHvluciRT4", as a template. The PCR product was cloned into the NotI window of pSeV18+ to obtain a recombinant Sendai virus vector to which the luciferase gene is inserted. Then, this recombinant vector was transfected into LLCMK2 cells, and after 3 cycles of freezing and thawing, the cells were inoculated into embryonated chicken eggs. Allantoic membranes of developing eggs were excised out, twice washed with cold PBS(−), and, after the addition of lysis buffer (Picagene WAKO) (25 µl) and thorough mixing, centrifuged at 15,000 rpm for 2 min. To the supernatant (5 µl each) was added the substrate (IATRON) (50 µl), and the mixture was dispensed into each well of a 96-well plate. Fluorescent intensity was measured with a luminometer (Luminous CT-9000D, DIA-IATRON), and the enzyme activity was expressed as counts per second (CPS). As a result, an extremely high luciferase activity was detected. The egg grown recombinant virus was purified by passaging once again in eggs, so that the stock virus did not contain helper vaccinia virus. This stock virus was then used to infect CV-1 cells and examine luciferase expression in these cells. As shown in Table 6, again, extremely high luciferase activity was detected for infected CV-1 cells at 24-h postinfection (Table 6). In these experiments, Sendai virus which did not carry the luciferase gene was used as control (represented by "SeV" in the table). Results obtained from two clones are shown in the table.

TABLE 6

| | Fluorescence intensity (counts/10 sec) | |
| --- | --- | --- |
| | Allantoic membrane | CV-1 (24 h postinfection) |
| Luc/SeV | 669187 | |
| | 2891560 | 8707815 |
| SeV | 69 | 48 |
| | 23 | 49 |

By the present invention, a system for efficient reconstitution of viral particles from Sendai viral cDNAs has been established, enabling the gene manipulation of Sendai virus to produce the recombinant Sendai virus comprising a genome with a desired foreign gene inserted or a desired gene deleted or inactivated, but retaining the disseminative capability.

What is claimed is:

1. A recombinant Sendai viral vector containing a Sendai viral genome in which at least one gene encoding a Sendai viral protein selected from the group consisting of NP, P, and L proteins is deleted or inactivated while all other Sendai virus genes, other than genes encoding NP, P, and L proteins, are retained, further wherein a foreign gene capable of being expressed in hosts is inserted in the Sendai viral genome between the R1 and R2 sequences.

2. The recombinant Sendai viral vector of claim 1, wherein the NP gene is deleted or inactivated.

3. The recombinant Sendai viral vector of claim 1, wherein the P gene is deleted or inactivated.

4. The recombinant Sendai viral vector of claim 1, wherein the L gene is deleted or inactivated.

5. An RNA molecule comprising RNA contained in a recombinant Sendai viral vector comprising a Sendai viral genome in which at least one gene encoding a Sendai viral protein selected from the group consisting of NP, P, and L proteins is deleted or inactivated while all other Sendai virus genes, other than genes encoding NP, P, and L proteins, are retained.

6. An RNA molecule comprising cRNAs of RNAs contained in a recombinant Sendai viral vector comprising a Sendai viral genome, wherein at least one gene encoding a Sendai viral protein selected from the group consisting of NP, P, and L proteins is deleted or inactivated while all other Sendai virus genes, other than genes encoding NP, P, and L proteins, are retained.

7. A kit comprising:
   i. a DNA molecule containing a template cDNA capable of transcribing RNA of claim 5 or 6, and
   ii. a unit capable of transcribing said RNA with said DNA as template in vitro or intracellularly.

8. A kit comprising:
   i. a cell expressing Sendai viral proteins NP, P, and L, and
   ii. the RNA molecule of claim 5 or 6.

9. The kit of claim 8, wherein the cell does not express heterologous DNA-dependent RNA polymerase.

10. A method for producing a recombinant Sendai viral vector comprising a Sendai viral genome in which at least one gene encoding a Sendai viral protein selected from the group consisting of NP, P, and L proteins is deleted or inactivated while all other Sendai virus genes, other than genes encoding NP, P, and L proteins, are retained, said method comprising the step of transfecting RNA of claim 5 or 6 to a cell wherein the cell expresses Sendai viral proteins NP, P, and L.

11. The method of claim 10, wherein the cell does not express heterologous DNA-dependent RNA polymerase.

12. A kit consisting of the following three components:
   i. a cell expressing Sendai viral proteins NP, P, and L;
   ii. a DNA molecule containing a template cDNA capable of transcribing RNA or cRNA of claim 5 or 6; and
   iii. a unit capable of transcribing said RNA with said DNA as template in vitro or intracellularly.

13. A method for producing a recombinant Sendai viral vector comprising a Sendai viral genome in which at least one gene encoding a Sendai viral protein selected from the group consisting of NP, P, and L proteins is deleted or inactivated while all other Sendai virus genes, other than genes encoding NP, P, and L proteins, are retained, said method comprising the step of introducing into a cell expressing Sendai viral proteins NP, P, and L a DNA molecule containing a template cDNA capable of transcribing RNA of claim 5 or 6, and a unit capable of transcribing said RNA with said DNA as a template intracellularly.

14. The method of claim 13, wherein the vector is produced entirely without the use of a helper virus.

15. A method for producing a foreign protein, comprising a process of infecting a host cell with a recombinant Sendai viral vector containing a Sendai viral genome carrying a foreign gene, wherein at least one gene encoding a Sendai viral protein selected from the group consisting of NP, P, and L proteins is deleted or inactivated while all other Sendai virus genes, other than genes encoding NP, P, and L proteins, are retained, and recovering the expressed foreign proteins, wherein said host cell is a tissue culture cell.

16. A cell culture medium or allantoic fluid containing expressed foreign proteins and Sendai virus particles or parts thereof, obtainable by:
   i. initially transfecting a recombinant Sendai viral vector containing a Sendai viral genome carrying a foreign gene, wherein at least one gene encoding a Sendai viral protein selected from the group consisting of NP, P, and L proteins is deleted or inactivated while all other Sendai virus genes, other than genes encoding NP, P, and L proteins, are retained, to a first host cell, wherein said foreign gene integrated therein encodes a foreign protein;
   ii. allowing said recombinant Sendai viral vector to disseminate to other host cells in the cell culture medium or around the allantoic fluid following said initial transfection of said recombinant Sendai viral vector into said host cells;
   iii. allowing said host cells to express said foreign protein; and
   iv. recovering said culture medium or allantoic fluid.

17. A DNA molecule for expressing a protein encoded by a foreign DNA integrated into a Sendai viral vector DNA, said Sendai viral vector DNA comprising:
   i. a promoter;
   ii. a cDNA encoding an RNA molecule corresponding to a Sendai viral genome in which at least one gene encoding a Sendai viral protein selected from the group consisting of NP, P, and L proteins, is deleted or inactivated, wherein all other Sendai virus genes, other than genes encoding NP, P, and L proteins, are retained; and
   iii. DNA encoding a foreign DNA, wherein said foreign DNA is integrated within said Sendai viral genome and the Sendai viral genome containing said foreign DNA is inserted downstream of said promoter in an orientation for transcribing an antisense RNA of both said Sendai viral genome and said foreign DNA.

18. An RNA molecule comprising RNA contained in a recombinant Sendai viral vector comprising a Sendai viral genome carrying a foreign gene, wherein at least one gene encoding a Sendai viral protein selected from the group consisting of NP, P, and L proteins, is deleted or inactivated while all other Sendai virus genes, other than genes encoding NP, P, and L proteins, are retained.

19. An RNA molecule comprising cRNAs of RNAs contained in a recombinant Sendai viral vector comprising a Sendai viral genome carrying a foreign gene, wherein at least one gene encoding a Sendai viral protein selected from the group consisting of NP, P, and L proteins, is deleted or inactivated while all other Sendai virus genes, other than genes encoding NP, P, and L proteins, are retained.

20. A kit comprising:
   i. a DNA molecule containing a template cDNA capable of transcribing RNA of claim 18 or 19, and
   ii. a unit capable of transcribing said RNA with said DNA as template in vitro or intracellularly.

21. A kit comprising:
   i. a cell expressing Sendai viral proteins NP, P, and L, and
   ii. the RNA molecule of claim 18 or 19.

22. The kit of claim 21, wherein the cell does not express heterologous DNA-dependent RNA polymerase.

23. A method for producing a recombinant Sendai viral vector comprising a Sendai viral genome carrying a foreign gene, wherein at least one gene encoding a Sendai viral protein selected from the group consisting of NP, P, and L proteins, is deleted or inactivated while all other Sendai virus genes, other than genes encoding NP, P, and L proteins, are retained, said method comprising the step of transfecting RNA of claim 18 or 19 to a cell wherein the cell expresses Sendai viral proteins NP, P, and L.

24. The method of claim 23, wherein the cell does not express heterologous DNA-dependent RNA polymerase.

25. A kit consisting of the following three components:
   i. a cell expressing Sendai viral proteins NP, P, and L;
   ii. a DNA molecule containing a template cDNA capable of transcribing RNA or cRNA of claim 18 or 19; and
   iii. a unit capable of transcribing said RNA with said DNA as template in vitro or intracellularly.

26. A method for producing a recombinant Sendai viral vector comprising a Sendai viral genome carrying a foreign gene, wherein at least one gene encoding a Sendai viral protein selected from the group consisting of NP, P, and L proteins, is deleted or inactivated while all other Sendai virus genes, other than genes encoding NP, P, and L proteins, are retained, said method comprising the step of introducing into a cell expressing Sendai viral proteins NP, P, and L a DNA molecule containing a template cDNA capable of transcribing RNA of claim 18 or 19, and a unit capable of transcribing said RNA with said DNA as a template intracellularly.

27. The method of claim 26, wherein the vector is produced entirely without the use of a helper virus.

28. The recombinant viral vector of claim 1 wherein the foreign gene is inserted in the Sendai viral genome prior to the ORF of the NP.

\* \* \* \* \*